United States Patent [19]

Kluge et al.

[11] 4,244,961
[45] Jan. 13, 1981

[54] 1-OXA-3,8-DIAZASPIRO[4.5]DECAN-2-ONES ANTIHYPERTENSIVE AGENTS

[75] Inventors: Arthur F. Kluge, Los Altos; Stefan H. Unger, Palo Alto, both of Calif.

[73] Assignee: Syntex (U.S.A.) Inc., Palo Alto, Calif.

[21] Appl. No.: 955,033

[22] Filed: Oct. 26, 1978

[51] Int. Cl.³ ............... A61K 31/445; C07D 498/10
[52] U.S. Cl. ............... 424/267; 260/326.16; 260/340.3; 260/348.63; 546/16; 546/19; 546/186; 546/242; 546/268
[58] Field of Search .......................... 546/19; 424/267

[56] References Cited

U.S. PATENT DOCUMENTS

| 3,399,192 | 8/1968 | Regnier et al. ............ 546/19 X |
| 3,577,425 | 5/1971 | Nakanishi et al. ............ 546/19 |
| 3,594,386 | 7/1971 | Regnier et al. ............ 546/19 |

FOREIGN PATENT DOCUMENTS

| 708051 | 4/1968 | Belgium . |
| 2163000 | 6/1972 | Fed. Rep. of Germany ............ 546/19 |

OTHER PUBLICATIONS

*Chemical Abstracts*, 71:91359d (1969) [Regnier, G. et al., Chim. Ther., 1969, 4(3), 185–194].
*Chemical Abstracts*, 78:71968t (1973) [Maillard, J. et al., Chim. Ther., 1972, 7(6), 458–466].
*Chemical Abstracts*, 81:105368b (1974) [Maillard, J. et al., Eur. J. Med. Chem.-Chim. Ther., 1974, 9(2), 128–132].

*Primary Examiner*—Henry R. Jiles
*Assistant Examiner*—Richard A. Schwartz
*Attorney, Agent, or Firm*—Tom M. Moran; Gerard A. Blaufarb

[57] ABSTRACT

Compounds of the formula

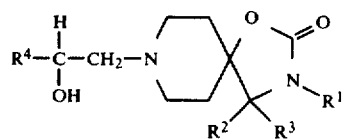

wherein $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety and $R^4$ is selected from the group having the formula

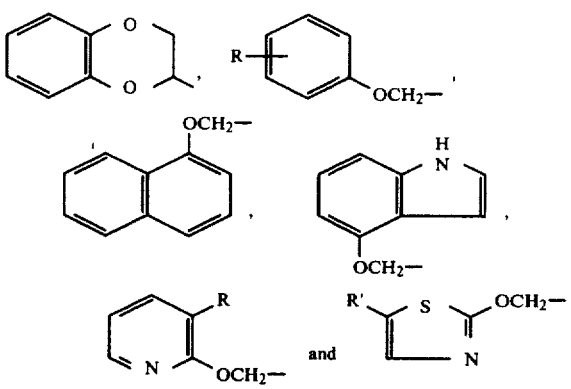

where R is $C_1$ to $C_8$ alkyl, $C_1$ to $C_8$ alkoxy, halo, cyano, AlkNHC(O)— or AlkC(O)NH— and R' is Alk NHC(O) or Alk C(O)NH where Alk is $C_1$ to $C_6$ alkyl or the group 2-(endobicyclo[3.1.0]hexyl)ethyl. Methods for preparing the compounds are disclosed. The compounds are useful for the treatment of hypertension and cardiac disorders.

32 Claims, 2 Drawing Figures

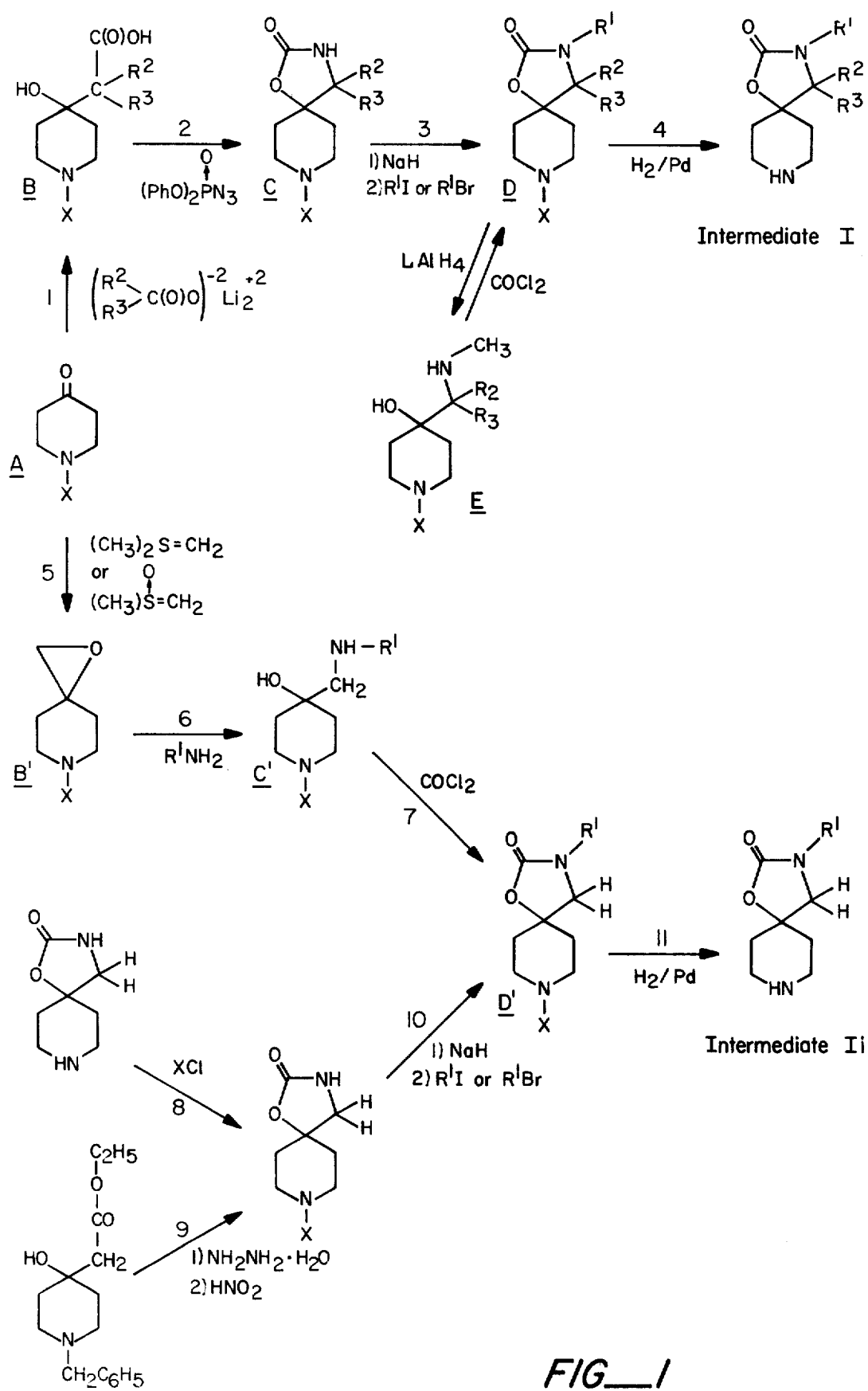
FIG__1

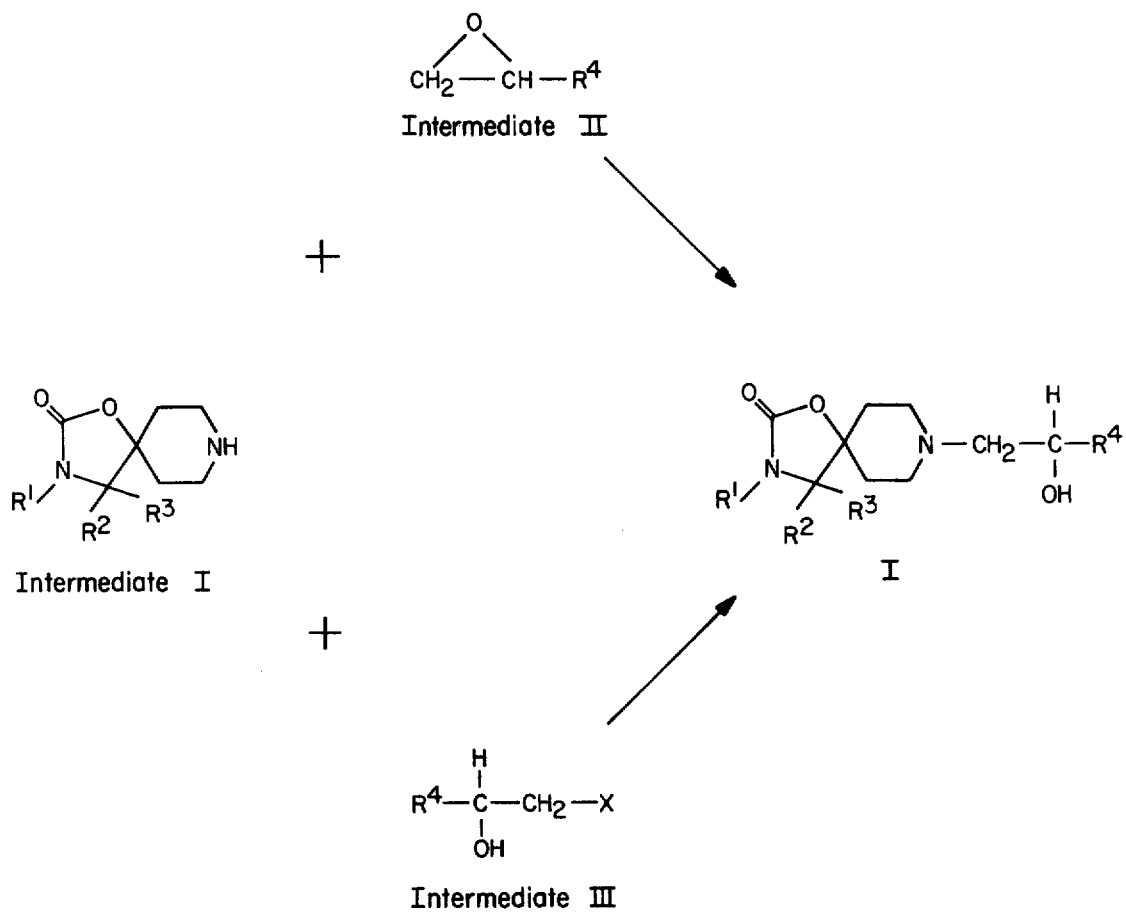
FIG_2

1-OXA-3,8-DIAZASPIRO[4.5]DECAN-2-ONES ANTIHYPERTENSIVE AGENTS

FIELD OF THE INVENTION

This invention relates to 8-(3-aryloxy-2-hydroxypropyl)-1-oxa-3,8-diazaspiro[4.5]decan-2-ones and pharmaceutically acceptable, nontoxic salts thereof and the methods for preparing these compounds. This invention further relates to 1-oxa-3,8-diazaspiro[4.5]decan-2-ones optionally substituted at positions 3, 4 and 8 and methods for preparing these compounds. This invention also relates to pharmaceutical compositions comprising one or more of the above compounds and to methods for treating hypertension and cardiac disorders in mammals.

DESCRIPTION OF PRIOR ART

Hypertension is a condition in which the pressure of the blood in the arteries is higher than normal. The definition of what is normal depends on the age of the individual, with the normal value increasing with age. For a young adult it is about 120/80, the higher figure representing the pressure (in millimeters of mercury) during systole, that is, when the heart is contracting and forcing blood into the arteries. The lower figure is the diastolic blood pressure or the pressure between contractions.

The following are among the drugs presently used to relieve hypertension: diuretics, which increase the excretion of salt and water (thus depleting blood volume), the sulfonamides, spironolactones, and furosemides; agents that act directly on the blood vessels to produce dilation, hydralazine and minoxidil; agents that produce vasodilation by counteracting the vasoconstricting action of the sympathetic nervous system, guanethidine, bethanidine, debrisoquine, and reserpine; and agents to decrease renin production by the kidney and thus decrease constriction of the blood vessels. Some of the drugs that are thought to decrease renin act in more than one way. This is true for reserpine, for example, and for methyldopa, which also acts through the nervous system. Propanolol may be given in combination with certain of these other drugs in order to counteract their side effects, and may have the additional effect of lowering renin output.

Therapy for combatting hypertension usually includes treatment with one or more of the above drugs, often in conjunction with a weight-reducing diet if the patient is overweight. Diets are rarely considered enjoyable, and many of the drugs are associated with side effects such as weakness or drowsiness and, in some cases, impotence. These factors, accompanied by the complicated schedules that are common when two or more drugs are prescribed as well as the fact that the treatment, which must often be continued for life, can have high cost over long periods of time leads to a diminishing acceptance of the therapy programs.

There is therefore a need for an effective antihypertensive agent exhibiting diminished side-effects when compared to presently existing agents.

SUMMARY

In summary, the compounds in accordance with the present invention can be represented by the following generic formula:

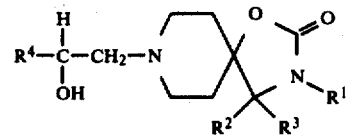

wherein $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety and $R^4$ is selected from the group having the formula

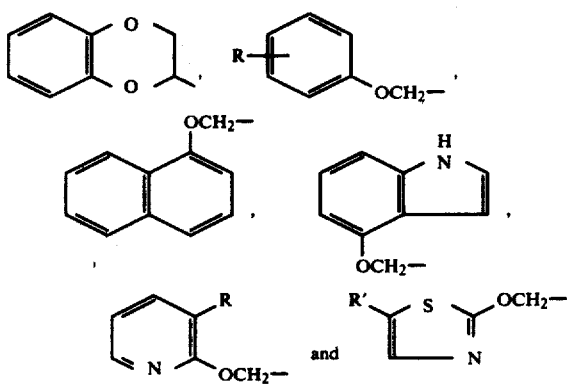

where R is $C_1$ to $C_8$ alkyl, $C_1$ to $C_8$ alkoxy, halo, cyano, AlkNHC(O)— or AlkC(O)NH— and R' is Alk NHC(O) or Alk C(O)NH— where Alk is $C_1$ to $C_6$ alkyl or the group 2-(endobicyclo[3.1.0]hexyl)ethyl.

Also encompassed within the present invention are the pharmaceutically acceptable, non-toxic salts of the above compounds of formula I.

The process of preparing the compounds of the present invention of formula I comprises treating a compound of the formula

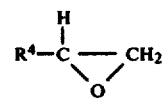

wherein $R^4$ is selected from the group having the formula

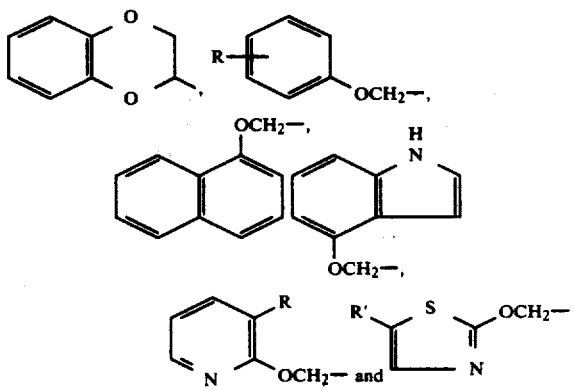

wherein R to $C_1$ to $C_8$ alkyl, $C_1$ to $C_8$ alkoxy, halo, cyano, AlkNHC(O)— or AlkC(O)NH— and R' is Alk NHC(O)— or Alk C(O)NH— where Alk is $C_1$ to $C_6$ alkyl or the group 2-(endobicyclo[3.1.0]hexyl)ethyl, with a compound of the formula:

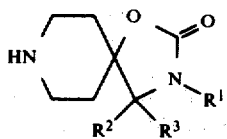

wherein $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety.

The pharmaceutical compositions of the present invention include both solids or powders and solutions comprising one or more of the compounds of the present invention in combination with a suitable pharmaceutical solvent or dispersant, i.e., sterile water or pharmaceutical solid excipients.

The compounds, compositions and methods of the present invention herein before disclosed will become more readily apparent from the following description in connection with the accompanying drawings in which:

FIG. 1 is a reaction sequence illustrative of the preparation of the intermediate compounds of the present invention; and FIG. 2 is a reaction sequence illustrative of the preparation of the compounds of the present invention of formula I.

DESCRIPTION OF THE PREFERRED EMBODIMENTS

The compounds of the present invention of formula I are, subgenerically represented by the formulas described below.

1.

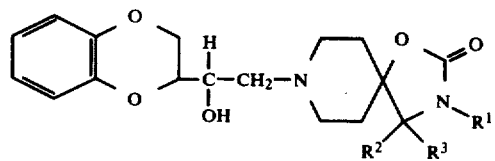

II wherein $R^1$, $R^2$ and $R^3$ are the same or different and are hydrogen, $C_1$ to $C_6$ alkyl, $C_6$ to $C_{14}$ carboxylic aryl or aralkyl of 1 to 6 carbon atoms in the alkyl moiety and 6 to 12 carbon atoms in carbocyclic aryl moiety and pharmaceutically acceptable, non-toxic salts thereof.

In the compounds of the present invention of formula II, $R^1$, $R^2$ and $R^3$ are the same or different and are preferably hydrogen; $C_1$ to $C_4$ alkyl, most preferably methyl, ethyl or i-propyl; $C_6$ to $C_{12}$ carbo monocyclic or bicyclic aryl, most preferably phenyl or naphthyl optionally mono- or disubstituted with methyl or ethyl; or aralkyl of 1 to 4 carbon atoms in the alkyl moiety, most preferably —$CH_2$— or —$CH_2$—$CH_2$— and 6 to 10 carbon atoms in the aryl moiety, most preferably phenyl or 1-naphthyl, i.e., the groups $PhCH_2$—, $PhCH_2CH_2$—, $NaphCH_2$— or $NaphCH_2CH_2$— where Ph is phenyl and Naph is naphthyl.

Particularly preferred compounds of the present invention of formula II are:

8-[2-(1,4-benzodioxan-2-yl)-2-hydroxyethyl]-1-oxa-3,8-diazaspiro[4.5]decan-2-one;

3-methyl-8-[2-(1,4-benzodioxan-2-yl)-2-hydroxyethyl]-1-oxa-3,8-diazaspiro[4.5]decan-2-one;

3-ethyl-8-[2-(1,4-benzodioxan-2-yl)-2-hydroxyethyl]-1-oxa-3,8-diazaspiro[4.5]decan-2-one;

3-i-propyl-8-[2-(1,4-benzodioxan-2-yl)-2-hydroxyethyl]-1-oxa-3,8-diazaspiro[4.5]decan-2-one; and 4-ethyl-8-[2-(1,4-benzodioxan-2-yl)-2-hydroxyethyl]-1-oxa-3,8-diazaspiro[4.5]decan-2-one.

2.

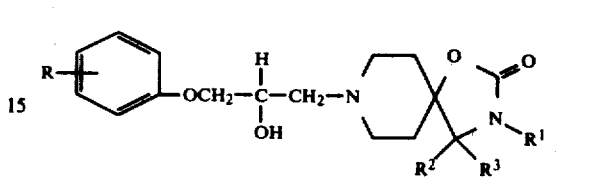

III wherein R is hydrogen $C_1$ to $C_8$ alkoxy, halo, cyano, AlkNHC(O)— or AlkC(O)NH—, wherein Alk is $C_1$ to $C_6$ alkyl. $R^1$, $R^2$ and $R^3$ are the same or different and are hydrogen, $C_1$ to $C_6$ alkyl, $C_6$ to $C_{14}$ carboxyclic aryl or aralkyl of 1 to 6 carbon atoms in the alkyl moiety and 6 to 12 carbon atoms in carbocyclic aryl moiety and pharmaceutically acceptable, non-toxic salts thereof.

In the compounds of the present invention of formula III, R is preferably hydrogen; $C_1$ to $C_4$ alkyl, most preferably, methyl, ethyl or i-propyl; $C_1$ to $C_4$ alkoxy, most preferably methoxy, ethoxy or i-propoxy; fluoro, chloro or bromo, most preferably chloro; AlkNHC(O)—, or AlkC(O)NH— where Alk is $C_1$ to $C_4$ alkyl, most preferably methyl, ethyl or i-propyl. $R^1$, $R^2$ and $R^3$ are the same or different and are preferably hydrogen; $C_1$ to $C_4$ alkyl, most preferably methyl, ethyl or i-propyl; $C_6$ to $C_{12}$ carbo monocyclic or bicyclic aryl, most preferably phenyl or naphthyl optionally monosubstituted or disubstituted with methyl or ethyl; or aralkyl of 1 to 4 carbon atoms in the alkyl moiety, most preferably —$CH_2$— or —$CH_2$—$CH_2$— and 6 to 10 carbon atoms in the aryl moiety, most preferably phenyl or 1-naphthyl, i.e., the groups $PhCH_2$—, $PhCH_2CH_2$—, $NaphCH_2$— or $NaphCH_2CH_2$— where Ph is phenyl and Naph is naphthyl.

Particularly preferred compounds of the present invention of formula III are:

8-[3-(2-methoxyphenoxy)-2-hydroxypropyl]-1-oxa-3,8-diazaspiro[4.5]decan-2-one;

3-methyl-8-[3-(2-methoxyphenoxy)-2-hydroxypropyl]-1-oxa-3,8-diazaspiro[4.5]decan-2-one;

3-ethyl-8-[3-(2-methoxyphenoxy)-2-hydroxypropyl]-1-oxa-3,8-diazaspiro[4.5]decan-2-one; and 3-isopropyl-8-[3-(2-methoxyphenoxy)-2-hydroxypropyl]-1-oxa-3,8-diazaspiro[4.5]decan-2-one.

3.

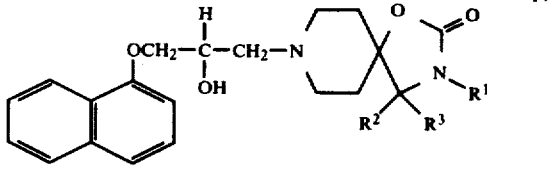

IV wherein $R^1$, $R^2$ and $R^3$ are the same or different and are hydrogen, $C_1$ to $C_6$ alkyl, $C_6$ to $C_{14}$ carboxyclic aryl or aralkyl of 1 to 6 carbon atoms in the alkyl moiety and 6 to 12 carbon atoms in carbocyclic aryl moiety and pharmaceutically acceptable, non-toxic salts thereof.

In the compounds of the present invention of formula IV, $R^1$, $R^2$ and $R^3$ are the same or different and are preferably hydrogen; $C_1$ to $C_4$ alkyl, most preferably methyl, ethyl or i-propyl; $C_6$ to $C_{12}$ carbo monocyclic or bicyclic aryl, most preferably phenyl or naphthyl optionally mono- or disubstituted with methyl or ethyl; or aralkyl of 1 to 4 carbon atoms in the alkyl moiety, most preferably —CH₂— or —CH₂—CH₂— and 6 to 10 carbon atoms in the aryl moiety, most preferably phenyl or 1-naphthyl, i.e., the groups PhCH₂—, PhCH₂CH₂—, NaphCH₂— or NaphCH₂CH₂— where Ph is phenyl and Naph is naphthyl.

Particularly preferred compounds of the present invention of formula IV are:

8-[3-(1-naphthyloxy)-2-hydroxypropyl]-1-oxa-3,8-diazaspiro[4.5]decan-2-one;

3-methyl-8-[3-(1-naphthyloxy)-2-hydroxypropyl]-1-oxa-3,8-diazaspiro[4.5]decan-2-one; and 3-ethyl-8-[3-(1-naphthyloxy)-2-hydroxypropyl]-1-oxa-3,8-diazaspiro[4.5]decan-2-one.

4.  V

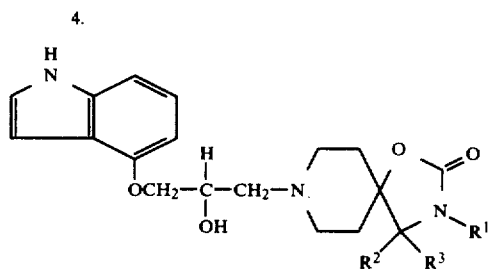

wherein $R^1$, $R^2$ and $R^3$ are the same or different and are hydrogen, $C_1$ to $C_6$ alkyl, $C_6$ to $C_{14}$ carboxyclic aryl or aralkyl of 1 to 6 carbon atoms in the alkyl moiety and 6 to 12 carbon atoms in carbocyclic aryl moiety and pharmaceutically acceptable, non-toxic salts thereof.

In the compounds of the present invention of formula V, $R^1$, $R^2$ and $R^3$ are the same or different and are preferably hydrogen; $C_1$ to $C_4$ alkyl, most preferably methyl, ethyl or i-propyl; $C_6$ to $C_{12}$ carbo monocyclic or bicyclic aryl, most preferably phenyl or naphthyl optionally monosubstituted or disubstituted with methyl or ethyl; or aralkyl of 1 to 4 carbon atoms in the alkyl moiety, most preferably —CH₂— or —CH₂—CH₂— and 6 to 10 carbon atoms in the aryl moiety, most preferably phenyl or 1-naphthyl, i.e., the groups PhCH₂—, PhCH₂CH₂—, NaphCH₂— or NaphCH₂CH₂— where Ph is phenyl and Naph is naphthyl.

Particularly preferred compounds of the present invention of formula V are:

8-[3-(4-indolyloxy)-2-hydroxypropyl]-1-oxa-3,8-diazaspiro[4.5]decan-2-one;

3-methyl-8-[3-(4-indolyloxy)-2-hydroxypropyl]-1-oxa-3,8-diazaspiro[4.5]decan-2-one; and 3-ethyl-8-[3-(4-indolyloxy)-2-hydroxypropyl]-1-oxa-3,8-diazaspiro[4.5]decan-2-one.

5.  VI

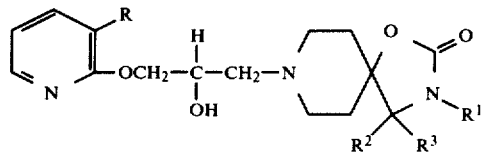

wherein R is hydrogen, $C_1$ to $C_8$ alkoxy, halo, cyano, AlkNHC(O)— or AlkC(O)NH—, wherein Alk is $C_1$ to $C_6$ alkyl. $R^1$, $R^2$ and $R^3$ are the same or different and are hydrogen, $C_1$ to $C_6$ alkyl, $C_6$ to $C_{14}$ carboxyclic aryl or aralkyl of 1 to 6 carbon atoms in the alkyl moiety and 6 to 12 carbon atoms in carbocyclic aryl moiety and pharmaceutically acceptable, non-toxic salts thereof.

In the compounds of the present invention of formula VI, R is preferably hydrogen or cyano, most preferably cyano. $R^1$, $R^2$ and $R^3$ are the same or different and are preferably hydrogen; $C_1$ to $C_4$ alkyl, most preferably methyl, ethyl or i-propyl; $C_6$ to $C_{12}$ carbo monocyclic or bicyclic aryl, most preferably phenyl or naphthyl optionally monosubstituted or disubstituted with methyl or ethyl; or aralkyl of 1 to 4 carbon atoms in the alkyl moiety, most preferably —CH₂— or —CH₂—CH₂— and 6 to 10 carbon atoms in the aryl moiety, most preferably phenyl or 1-naphthyl, i.e., the groups PhCH₂—, PhCH₂CH₂—, NaphCH₂— or NaphCH₂CH₂— where Ph is phenyl and Naph is naphthyl. Particularly preferred compounds of the present invention of formula VI are:

8-[3-(3-cyano-2-pyridyloxy)-2-hydroxypropyl]-1-oxa-3,8-diazaspiro[4.5]decan-2-one;

3-methyl-8-[3-(3-cyano-2-pyridyloxy)-2-hydroxypropyl]-1-oxa-3,8-diazaspiro[4.5]decan-2-one; and 3-ethyl-8-[3-(3-cyano-2-pyridyloxy)-2-hydroxypropyl]-1-oxa-3,8-diazaspiro[4.5]decan-2-one;

6.  VII

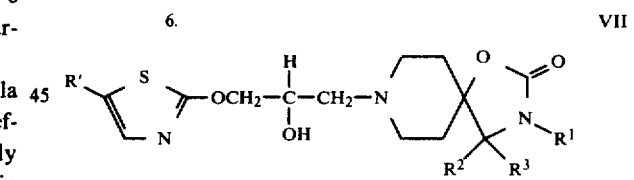

wherein R' is AlkNHC(O)— or AlkC(O)NH—, wherein Alk is $C_1$ to $C_6$ alkyl or the group 2-(endobicyclo[3.1.0]hexyl)ethyl. $R^1$, $R^2$ and $R^3$ are the same or different and are hydrogen, $C_1$ to $C_6$ alkyl, $C_6$ to $C_{14}$ carboxyclic aryl or aralkyl or 1 to 6 carbon atoms in the alkyl moiety and 6 to 12 carbon atoms in carbocyclic aryl moiety and pharmaceutically acceptable, non-toxic salts thereof.

In the compounds of the present invention of formula VII, R' is preferably AlkNHC(O)— or AlkC(O)NH— where Alk is $C_1$ to $C_4$ alkyl or the group 2-(endobicyclo[3.1.0]hexyl)ethyl, most preferably the group 2-(endobicyclo[3.1.0]hexyl)ethyl, methyl, ethyl or i-propyl. $R^1$, $R^2$ and $R^3$ are the same or different and are preferably hydrogen; $C_1$ to $C_4$ alkyl, most preferably methyl, ethyl or i-propyl; $C_6$ to $C_{12}$ carbo monocyclic or bicyclic aryl, most preferably phenyl or naphthyl optionally monosubstituted or disubstituted with methyl or ethyl; or aralkyl of 1 to 4 carbon atoms in the alkyl moiety, most preferably —CH$_2$— or —CH$_2$—CH$_2$— and 6 to 10 carbon atoms in the aryl moiety, most preferably phenyl or 1-naphthyl, i.e., the groups PhCH$_2$—, PhCH$_2$CH$_2$—, NaphCH$_2$— or NaphCH$_2$CH$_2$— where Ph is phenyl and Naph is naphthyl.

Particularly preferred compounds of the present invention of formula VII are:

8-[3-(5-[2-(endobicyclo[3.1.0]hexyl)ethyl]carboxamido-2-thiazolyloxy)-2-hydroxypropyl]-1-oxa-3,8-diazaspiro[4.5]decan-2-one; and 3-methyl-8-[3-(5-[2-(endobicyclo[3.1.0]hexyl)ethyl]-carboxamido-2-thiazolyloxy)-2-hydroxypropyl]-1-oxa-3,8-diazaspiro[4.5]decan-2-one.

The preferred pharmaceutically acceptable salts are hydrogen addition salts of bromide, sulfate, lactate, tartrate, succinate and especially chloride and maleate. Thus, the preferred salts are the preferred anion addition salts of formula I and correspondingly the particularly preferred salts are the preferred hydrogen-anion addition salts of the preferred and particularly preferred compounds of formula I and especially the hydrochloride and maleate salts.

Referring now to FIG. 1, the intermediate compounds useful in the preparation of the compounds of formula I are prepared by first treating (step 1.) N-carbobenzyloxy- or N-benzyl-4-piperidone, compound A, dissolved or dispersed in an inert solvent with a alkali metal salt of an R$^2$,R$^3$-substituted carboxylic acid, typically a lithium salt, in an inert atmosphere, at −70° to −75° for a time sufficient to complete the reaction, typically 5 minutes to 5 hours. Mole ratios of the alkali metal salt:N-substituted piperidone may range from 1:5 to 5:1, preferably 1:1. The resulting (N-protected 4-hydroxypiperidin-4-yl)-R$^2$,R$^3$-substituted acetic acid, compound B, is next treated (step 2.) with diphenylphosphoryl azide in a modification of the Curtius Rearrangement, forming the (not isolated) acyl azide, which, after thermal rearrangement to the isocyanate, cyclizes to form a 4,4-R$^2$,R$^3$-disubstituted-8-carbobenzyloxy- or -benzyl-1-oxa-3,8-diazaspiro[4.5]decan-2-one, compound C. This Rearrangement is a well-known prior art technique and has been described with particularity in, for example, Lebel, et al, *Synthesis*, 1973, 678.

The N-protected 1-oxa-3,8-diazaspiro[4.5]decan-2-one (Compound C) is reacted with an alkali metal hydride (step 3.1). This initial treatment is typically conducted at temperatures in the range of from about −30° to 30°, preferably from about −10° to 5° from about one minute to one hour, preferably from about five minutes to 20 minutes. An R$^1$ halide such as an alkyl chloride, bromide, or iodide typically dissolved in an inert organic solvent, is then added to the preceding mixture (step 3.2). Typically, this treatment is conducted at temperatures in the range of from about 25° to 45°, for from about one minute to three hours, preferably from about 10 to 30 minutes. Typically, mole ratios of alkali metal hydride:diazaspirodecanone of from about 1 to 5:1, preferably from about 1.0 to 1.3:1 are used, with mole ratios of compound C:R$^1$ halide being in the range of from about 1 to 5:1 preferably from about 1.0 to 1.3:1. Suitable alkali metal hydrides which can be used include, for example, sodium hydride, potassium hydride, lithium hydride, and the like. Suitable inert organic solvents which can be used include, for example, tetrahydrofuran, dioxane, dimethoxyethane, dimethylformamide and the like, and mixtures thereof. Both procedures of the treatment are conducted under anhydrous conditions, and preferably under an inert atmosphere (e.g. nitrogen). Compound D is preferably isolated before being used as starting material for the next step. Such isolation can be effected by conventional separation procedures such as, for example, precipitation with water, extraction, crystallization or chromatography. Specific illustrations of typical separation and isolation procedures can be had by reference to the appropriate Preparations, hereinbelow.

Intermediate I is formed from compound D by catalyzed hydrogenation (when X is benzyl, R$^1$ cannot be aralkyl and R$^2$ and/or R$^3$ cannot be carbocyclic aryl), step 4. Typically this reaction is carried out in an inert solvent at elevated pressures and temperatures, 20–100 psi and 30°–100°, preferably 55–65 psi and 45°–55°, for a time sufficient to complete the reaction, 10 minutes to 5 hours, typically 1 hour. When catalyzed hydrogenation is employed, any of the recognized metallic or metal oxide-supported or unsupported catalysts can be used, including platinum, platinum oxide, and palladium. Preferably palladium on carbon is used in the catalyzed reaction. Various inert solvents useful in the reduction include both polar and non-polar solvents such as the alcohols illustrated by methanol, ethanol and the like, the ethers illustrated by diethyl ether, dioxane and the like, and the esters illustrated by ethylacetate and the like.

Intermediate I is readily isolated from the reaction mass by any of the conventional methods indicated above.

As an alternate procedure for the preparation of Intermediate Ii(Intermediate I where R$^1$=R$^2$=hydrogen), trimethyl sulfonium or trimethyl sulfoxonium iodide is first treated with an alkali metal hydride thereby abstracting a proton from one methyl group and forming the dimethylmethylene homolog. Compound A, dispersed or dissolved in a suitable organic liquid, is added to the resulting reaction mixture (step 5) typically at about 0°–60° and, after a time sufficient to complete the reaction, usually 1 hour to 48 hours, the N-protected piperidine epoxide, compound B', is obtained. The epoxide ring is readily opened at elevated temperature by any R'-substituted amine (step C) forming a 1-carbobenzyloxy- or 1-benzyl-4-hydroxy-4-(R'aminomethyl)piperidine, Compound C'. Typical temperatures for such ring-opening reaction include 100°–200°, usually 150°–170°. The reaction is typically conducted in the absence of solvent. Compound C' is then treated with phosgene (step 7) in the presence of a suitable acid acceptor, thereby forming 3-R'-8-X-1-oxa-3,8-diazaspiro[4.5]decan-2-one, compound D'. This latter compound can be converted to Intermediate Ii by the hydrogenation process (step 11) described previously for compound D. As noted before in cases where R$^1$ is aralkyl, the blocking group X must be the radical carbobenzyloxy.

As alternate technique for the preparation of the immediate precursor to Intermediate Ii, compound D' can be prepared by treating 8-benzyl- or 8-carbobenzyloxy-1-oxa-3,8-diazaspiro[4.5]decan-2-one with an alkali metal hydride (Step 10.1) followed by a R$^1$ bromide or iodide (step 10.2) in a manner identical to that described above for treatment of compound C (step 3.). FIG. 1 illustrates the preparation of this compound by two alternate routes, from 1-oxa-3,8-diazaspiro[4.5]decan-2-one (step 8) and from ethyl (1-benzyl-4-hydroxypiperidene-4-yl)acetate (step 9). See Preparations 8 and 9 respectively. Reduction of compound D (X=benzyl, R$^1$=H, R$^2$ and R$^3$=H or alkyl) with lithium aluminum hydride gives compound E. Typically this reduction is accomplished at elevated temperatures, in an inert organic solvent, for example at 30°-100° in tetrahydrofuran, for a time sufficient to complete the reaction. Treatment of E with phosgene or diphenyl carbonate gives compound D ($R^1$=methyl). This reaction is conducted effectively at temperatures from 10° to 50°, preferably 20° in an inert organic solvent such as dichloromethane.

Referring now to FIG. 2, the compounds of the present invention of formula I can be conveniently prepared by treating the epoxy compounds, Intermediate II with the compounds, Intermediate I. Typically, this treatment is conducted in an inert organic solvent at temperatures in the range of from about −10° to 100°, preferably from about 10° to 50°, for from about one hour to 48 hours, preferably from about 3 to 18 hours. Typically, a mole ratio of Intermediate I:Intermediate II in the range of from about 1:1 to 1:10, preferably from about 1:1.5, is used. Suitable inert organic solvents which can be used include, for example, methanol, ethanol, monoglyme, toluene and the like and mixtures thereof. The resulting products of formula I can then be separated and isolated according to conventional procedures such as, for example, evaporation, crystallization, column chromatography, thin-layer chromatography, etc. Specific illustrations of typical separation and isolation procedures can be had by reference to the corresponding Examples, set forth hereinbelow.

As a further embodiment for the process of preparing the compounds of the present invention of formula I, FIG. 2 illustrates a further reaction sequence, again utilizing Intermediate I, but treating such with an $R^4$-substituted halo alcohol of the formula $R^4CH(OH)CH_2X$, where X is halogen selected from the group chloro or bromo. The reaction is typically conducted in an inert organic solvent in the presence of an acid acceptor such as trimethylamine, triethylamine, quinuclidine, 1,4-diaza-2,2,2-bicyclooctane, potassium carbonate and the like. Inert organic solvents may include, for example, dimethyl formamide, dimethylsulfoxide, monoglyme and the like. The compounds of formula I readily form from this reaction which typically is conducted at 20°-150° preferably 60°-100° for periods of from about 10 to about 48, preferably 14 to 24 hours. The products are isolated by conventional techniques as described above and in the Examples hereinbelow.

The compounds of the invention are also useful in the treatment of cardiac disorders in mammals.

The compounds of this invention are typically administered, both for the treatment of cardiac disorders and hypertension, in dosages of from about 0.01 to 5 mg per kg. of body weight. The precise effective dosage will, of course, vary depending upon the mode of administration, the condition being treated, and the host. Where the compounds are used to treat cardiac conditions the compounds are typically administered either orally or intravenously. Where the compounds are administered to treat hypertension the compounds are, for the sake of convenience, typically administered orally.

The compounds of the invention can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. In the case of the compounds of formula I, the compounds are typically administered as pharmaceutically acceptable salts. The pharmaceutical carrier can be either a solid material or liquid in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, pharmaceutical phosphate salts and the like.

The liquid compositions can, for example, be in the form of solutions, emulsions, suspensions, syrups, or elixirs and optionally can contain small quantities of preservatives and/or buffering agents, and preferably contain the therapeutic agent in convenient unit dosage concentrations.

The solid compositions can take the form of tablets, powders, capsules, pills and the like, preferably in unit dosage forms for simple administration or precise dosages. Suitable solid carriers include, for example, pharmaceutical grades of starch, lactose, sodium saccharine, sodium bisulfite and the like.

Also based on studies on related compounds, it can be predicted that a number of the present compounds will exhibit useful local anesthetic activity. Where the compounds are applied as local anesthetics, they can be administered topically, intradermally, or subcutaneously.

The compounds of formula I can be administered as racemic mixtures or they can be administered as resolved enantiomers or optical isomers. In some instances, one enantiomer or optical isomer exhibits a greater antihypertensive effect than does the other corresponding enantiomer or optical isomer.

As used in the specification and the appended claims, the following terms have the meaning indicated. The term "$C_1$ to $C_8$ alkyl" refers to a straight or branched chain monovalent substituent consisting solely of carbon and hydrogen, containing no unsaturation, and having from 1 to 8 carbon atoms. Examples of such alkyl groups are methyl, ethyl, n-propyl, i-propyl, n-butyl, t-butyl, n-hexyl, n-heptyl, n-octyl and the like. The term "$C_1$ to $C_8$ alkoxy" refers to 1 to 8 carbon-containing alkyl groups linked through an ether linkage, having the free valence from the ether oxygen. Examples of such groups include methoxy, ethoxy, n-propoxy, i-propoxy, n-butoxy, t-butoxy, n-hexoxy, n-heptoxy, n-octoxy, and the like. The term "halo" refers to fluoro, chloro, bromo and iodo. The term "aralkyl of 1 to 6 carbon atoms in the alkyl moiety and 6 to 12 carbon atoms in the carbocyclic aryl moiety" is defined as 1 to 6 carbon-containing alkyl groups (some of which are defined above) attached to a monocyclic or polycyclic aromatic ring or rings of 6 to 10 carbon atoms which are optionally substituted with one or two $C_1$ to $C_4$ alkyl groups. Illustrative of such are the groups $PhCH_2$—, $PhCH_2CH_2$—, $NaphCH_2CH_2$ and $NaphCH_2CH_2$— where Ph and Naph are phenyl and naphthyl respectively.

The term "pharmaceutically acceptable, non-toxic salts" is recognized in the art to designate addition salts formed from an acid that is physiologically innocuous when administered in a dosage and at an interval that is effective for the indicated therapeutic use of the parent compound. Typical pharmaceutically acceptable addition salts of the compounds of formula I include salts with inorganic acids such as hydrochloric acid, hydrobromic acid, sulfuric acid, nitric acid or phosphoric acid; and salts with organic acids such as acetic acid, propionic acid, lactic acid, succinic acid, malic acid, maleic acid, tartaric acid, citric acid, and the like.

All compounds of formula I possess at least one chiral center. Accordingly, the compounds of the invention may be prepared in either their optically active form or as a racemic mixture. Unless otherwise specified, the compounds described herein are all in the racemic form. However, the scope of the subject invention is not to be considered limited to the racemic form, but to encompass the individual optical isomers of the compounds of the present invention.

The compounds of formula II possess at least two chiral centers. Accordingly, compounds of this formula can be erythro or threo diastereoisomers. For each diastereoisomer the compounds of the invention can be prepared in either optically active form or as a racemic mixture. Unless otherwise specificied the compounds of formula II described herein are in the racemic form and are mixtures of the erythro and threo diastereoisomers.

In the cases were $R^2$ and $R^3$ are not identical, a further assymetric center is introduced into the compounds of formula I. In compounds bearing this additional assymetry, four discrete stereoisomers are possible (2 enantiomeric pairs). Additionally, in compounds of formula II where $R^2$ and $R^3$ are not identical there are three centers of assymetry, giving rise to a total of eight discrete stereoisomers. As in the case of the compounds with a single assymetric center, these multi-assymetrically centered compounds of formulas I (and II) may also have one enantiomer or optical isomer displaying enhanced physiologic activity over other enantiomeric or optically isomeric forms.

Where desired the individual diastereomeric and optically isomeric comounds can be isolated by conventional separation and purification procedures in the case of diastereomers and by conventional resolution procedures in the case of optical isomers (for example, by reacting the optical isomer mixtures with an optically active acid affording a mixture of optically isomeric salts of the compounds of formula I which can be resolved by conventional procedures (e.g. crystallization) into the respective (+) and (−) optically isomeric salts. Optimum physical, or physical-chemical, separation procedures and resolution procedures can be obtained by routine trial and error procedures well within the scope of those skilled in the art.

A further understanding of the invention can be had from the following non-limiting Preparations and Examples. As used hereinabove and below unless expressly stated to the contrary, all temperatures and temperature ranges refer to the Centigrade system and the terms ambient or room temperature refer to about 20° C. The term percent or (%) refers to weight percent and the term mole and moles refers to gram moles. The term equivalent refers to a quantity of reagent equal in moles to the moles of the preceding or succeeding reactant recited in that Preparation or Examples in the terms of moles of finite weight or volume. As noted earlier, compounds having assymetric centers and optical activity are isolated in their racemic form (±) unless otherwise indicated.

PREPARATION 1

1. To a 100 ml flask maintained under argon are added 2.22 g of diisopropylamine and 15 ml tetrahydrofuran. The contents of the flask are cooled to 0° and are maintained at that temperature. A solution of 1.5 M n-butyllithium (14.7 ml) is added and the solution is stirred for five minutes. Isobutyric acid (0.88 g) is added and the mixture is stirred for 15 minutes at 20°. The mixture is cooled to −70° and a solution of 2.33 g of N-carbobenzyloxy-4-piperidone in 5 ml tetrahydrofuran is added at such a rate that the temperature remains below −50°. The mixture is allowed to warm to room temperature and is poured into 150 ml diethyl ether. This solution is extracted with two 150 ml portions of 1 N hydrochloric acid, 50 ml of water, and 100 ml of 2% sodium hydroxide. The basic layer is acidified with 10 N hydrochloric acid and the resulting mixture is extracted with three 50 ml portions of diethyl ether. Evaporation of the ether affords an oil which is triturated with 50 ml hexane to give 1.65 g 2-(1-carbobenzyloxy-4-hydroxypiperidin-4-yl)-2-methylpropionic acid, an oil.

Similarly prepared are the following:
(from phenylacetic acid),
(1-carbobenzyloxy-4-hydroxypiperidin-4-yl)phenylacetic acid, an oil; and
(from 3-phenylpropionic acid),
2-(1-carbobenzyloxy-4-hydroxypiperidin-4-yl)-3-phenylpropionic acid, m.p. 166°–168.5°.

2. A mixture of 2.12 g diisopropylamine and 15 ml tetrahydrofuran is stirred under argon at 0°. To this solution is added over two minutes 14 ml of 1.5 M n-butyllithium. To this solution at 0° is added 0.6 g acetic acid. The mixture is stirred five minutes at 20° and then cooled to −70°. To this mixture is added a solution of 1.89 g N-benzyl-4-piperidone in 4 ml tetrahydrofuran. The mixture is allowed to warm to room temperature and poured into 50 ml 1% sodium hydroxide. This mixture is extracted with three 50 ml portions of diethyl ether. The aqueous phase is adjusted to pH 7.0 with 3 N hydrochloric acid and is extracted with five 40 ml portions of dichloroethane. Evaporation of the dichloromethane affords (1-benzyl-4-hydroxypiperidin-4-yl)acetic acid.

Similarly prepared are the following:
(from propionic acid),
2-(1-benzyl-4-hydroxypiperidin-4-yl)propionic acid;
(from butyric acid),
2-(1-benzyl-4-hydroxypiperidin-4-yl)butyric acid;
(from pentanoic acid),
2-(1-benzyl-4-hydroxypiperidin-4-yl)pentanoic acid; and
(from isobutyric acid),
2-(1-benzyl-4-hydroxypiperidin-4-yl)-2-methylpropionic acid.

PREPARATION 2

A mixture of 2-(1-carbobenzyloxy-4-hydroxypiperidin-4-yl)-2-methylpropionic acid, 1.29 g diphenylphosphoryl azide, 0.47 g of triethylamine, and 50 ml toluene is heated at reflux for 18 hours. Evaporation of solvent gives a residue which is taken up in 125 ml dichloromethane and is washed with 50 ml 1 N hydrochloric acid and 50 ml, 5% sodium bicarbonate. Evaporation of the solvent followed by trituration with diethyl ether affords 1.86 g 4,4-dimethyl-8-carbobenzyloxy-1-oxa-3,8-diazaspiro[4.5]decan-2-one, mp 208°–209°.

Similarly prepared are the following:
4-phenyl-8-carbobenzyloxy-1-oxa-3,8-diazaspiro[4.5]decan-2-one, mp 168°–169°; and
4-benzyl-8-carbobenzyloxy-1-oxa-3,8-diazaspiro[4.5]decan-2-one, mp 119°–121°.

PREPARATION 3

1. A mixture of 16.5 g 8-benzyl-1-oxa-3,8-diazaspiro[4.5]decan-2-one, 6.6 g, 50% suspension of sodium hydride in mineral oil, 15 g ethyl iodide and 70 ml N,N-dimethylformamide is heated at 90° for one hour. The mixture is poured into 150 ml water and the resulting mixture acidified with 10 N hydrochloric acid. The mixture is extracted with two 100 ml portions of hexane. The aqueous layer is basified with sodium hydroxide and extracted with three 75 ml portions of dichloromethane. Removal of solvent in vacuum affords a residue which when crystallized from heptane gives 3-ethyl-8-benzyl-1-oxa-3,8-diazaspiro[4.5]decan-2-one, mp 105°–106°.

Similarly prepared are the following:
(from methyl iodide),
3-methyl-8-benzyl-1-oxa-3,8-diazaspiro[4.5]decan-2-one, mp 137°–138°;
(from 1-bromopropane),
3-n-propyl-8-benzyl-1-oxa-3,8-diazaspiro[4.5]decan-2-one, mp 98°–99°;
(from 2-bromopropane),
3-isopropyl-8-benzyl-1-oxa-3,8-diazaspiro[4.5]decan-2-one, mp 120°–121°;
(from 4-bromobutane),
3-n-butyl-8-benzyl-1-oxa-3,8-diazaspiro[4.5]decan-2-one, mp 80.5°–81°; and
(from 2-bromoethylbenzene),
3-(2-phenethyl)-8-benzyl-1-oxa-3,8-diazaspiro[4.5]decan-2-one, mp 155°–157°.

2. A mixture of 9.1 g 8-carbobenzyloxy-1-oxa-3,8-diazaspiro[4.5]decan-2-one, 1.85 g, 57% suspension of sodium hydride in mineral oil, 6 ml methyl iodide and 45 ml N,N-dimethylformamide is heated one hour at 60°. The mixture is poured into 200 ml water and the resulting mixture extracted with three 100 ml portions of dichloromethane. The dichloromethane extracts are combined and evaporated to give a residue which is washed with three 100 ml portions of hexane and three 100 ml portions of water. This affords 8.95 g of 3-methyl-8-carbobenzyloxy-1-oxa-3,8-diazaspiro[4.5]decan-2-one, an oil; m/e=304 (M+).

Similarly prepared is (from benzyl bromide) 3-benzyl-8-carbobenzyloxy-1-oxa-3,8-diazaspiro[4.5]decan-2-one, an oil; m/e=380 (M+).

PREPARATION 4

1. A mixture of 4.54 g 4,4-dimethyl-8-carbobenzyloxy-1-oxa-3,8-diazaspiro[4.5]decan-2-one, 75 ml ethanol and 1 g 5% palladium on carbon is hydrogenated at 60 psi and 50° for one hour. Filtration and evaporation affords 2.65 g 4,4-dimethyl-1-oxa-3,8-diazaspiro[4.5]decan-2-one, mp 238°–240°.

Similarly prepared are the following:
4-phenyl-1-oxa-3,8-diazaspiro[4.5]decan-2-one, mp 38°–40°; and
4-benzyl-1-oxa-3,8-diazaspiro[4.5]decan-2-one, mp 237°–238°.

2. A mixture of 22.2 g 3-benzyl-8-carbobenzyloxy-1-oxa-3,8-diazaspiro[4.5]decan-2-one, 150 ml ethanol and 5 g, 5% palladium on barium sulfate is hydrogenated at 60 psi at room temperature for 90 minutes. After filtration and removal of solvent there is obtained 15.4 g of 3-benzyl-1-oxa-3,8-diazaspiro[4.5]decan-2-one, mp 69°–71°.

3. A mixture of 6.2 g 8-benzyl-1-oxa-3,8-diazaspiro[4.5]decan-2-one, 50 ml ethanol and 0.5 g, 10% palladium on carbon is hydrogenated at 60 psi and 50° for 18 hours. After filtration and removal of solvent there is obtained 4.2 g 1-oxa-3,8-diazaspiro[4.5]decan-2-one, mp 158°–161°.

Similarly prepared are the following:
3-methyl-1-oxa-3,8-diazaspiro[4.5]decan-2-one, mp 95°–96°;
3-ethyl-1-oxa-3,8-diazaspiro[4.5]decan-2-one, mp 55°–57°;
3-n-propyl-1-oxa-3,8-diazaspiro[4.5]decan-2-one, oil;
3-isopropyl-1-oxa-3,8-diazaspiro[4.5]decan-2-one, 41°–45°;
3-n-butyl-1-oxa-3,8-diazaspiro[4.5]decan-2-one, oil; and
3-(2-phenethyl)-1-oxa-3,8-diazaspiro[4.5]decan-2-one, mp 93°–95°.

PREPARATION 5 a. In a 250 ml flask under argon are mixed 1.2 g mineral oil-free sodium hydride, 11 g trimethylsulfoxonium iodide and 60 ml dimethylsulfoxide. The mixture is stirred for two hours and then is added 9.32 g N-carbobenzyloxy-4-piperidone, the stirring being continued at room temperature for 30 minutes, followed by 50° for one hour, then room temperature for 18 hours. The mixture is poured into 300 ml water and extracted with three 70 ml portions of diethyl ether. The combined diethyl ether extracts are washed with 50 ml water. Removal of solvent by evaporation affords 3.8 g of crude epoxide.

b. The product of step a. is mixed with 5 g. of aniline and the mixture heated at 160° for four hours. This mixture is cooled to room temperature and dissolved in 150 ml diethyl ether. The ether solution is extracted with two 40 ml portions of 1 N hydrochloric acid. The acid extract is basified with 20% sodium hydroxide and the resulting mixture extracted with three 50 ml portions of diethyl ether. Removal of the ether by evaporation yields a crude product which is filtered through 50 g silica gel with 150 ml, 40% diethyl ether-hexane, followed by 150 ml diethyl ether. Evaporation of the diethyl ether filtrate gives 2.2 g of 1-carbobenzyloxy-4-hydroxy-4-anilnomethylpiperidine, an oil, m/e=340.

Similarly prepared are the following:
(from 2-methoxyaniline),
1-carbobenzyloxy-4-hydroxy-4-(2-methoxyanilino)methylpiperidine;
(from 3-methylaniline),
1-carbobenzyloxy-4-hydroxy-4-(3-methoxyanilino)methylpiperidine; and
(from 4-chloroaniline),
1-carbobenzyloxy-4-hydroxy-4-(4-chloroanilino)methylpiperidine.

PREPARATION 6

To a mixture of 2.2 g 1-carbobenzyloxy-4-hydroxy-4-anilinomethylpiperidine, 3 ml triethylamine and 20 ml dichloromethane is added a solution of 3 g phosgene in 25 ml toluene. After 30 minutes the mixture is washed with 100 ml, 1 N hydrochloric acid. Removal of solvent by evaporation followed by recrystallization from diethyl ether-hexane affords 1.2 g of 3-phenyl-8-carbobenzyloxy-1-oxa-3,8-diazaspiro[4.5]decan-2-one, mp 100°–102°.

Similarly prepared are the following:
3-(2-methoxyphenyl)-8-carbobenzyloxy-1-oxa-3,8-diazaspiro[4.5]decan-2-one;

3-(3-methylphenyl)-8-carbobenzyloxy-1-oxa-3,8-diazaspiro[4.5]decan-2-one; and 3-(4-chlorophenyl)-8-carbobenzyloxy-1-oxa-3,8-diazaspiro[4.5]decan-2-one.

PREPARATION 7

A mixture of 3.4 g 3-phenyl-8-carbobenzyloxy-1-oxa-3,8-diazaspiro[4.5]decan-2-one, 50 ml ethanol and 0.4 g, 10% palladium on carbon is hydrogenated at room temperature and 60 psi for 6 hours. Filtration and removal of solvent affords 2.45 g 3-phenyl-1-oxa-3,8-diazaspiro[4.5]decan-2-one, a pasty solid; m/e=232 (M+).

Similarly prepared are the following:

3-(2-methoxyphenyl)-1-oxa-3,8-diazaspiro[4.5]decan-2-one;

3-(3-methylphenyl)-1-oxa-3,8-diazaspiro[4.5]decan-2-one; and 3-(4-chlorophenyl)-1-oxa-3,8-diazaspiro[4.5]decan-2-one.

PREPARATION 8

To a mixture of 9.5 g 1-oxa-3,8-diazaspiro[4.5]decan-2-one and 75 ml water, at 0°, are added 6.3 g sodium bicarbonate and 10.9 g benzyl chloroformate. The mixture is stirred 18 hours at 0°, acidified with 10 N hydrochloric acid and stirred four hours at room temperature. The mixture is extracted with three 50 ml portions of dichloromethane. Removal of solvent affords 14.4 g 8-carbobenzyloxy-1-oxa-3,8-diazaspiro[4.5]decan-2-one, mp 126°-128°.

PREPARATION 9 a. A mixture of ethyl (1-benzyl-4-hydroxypiperidin-4-yl)acetate [Helv. Chim. Acta, 51, 1184 (1958)] and 25 ml hydrazine hydrate is heated at reflux for ten minutes. 150 ml Ethanol is added and the reflux continued one hour. The solvent is removed at reduced pressure, the residue taken up in 100 ml ethanol and this solution mixed with 100 ml diethyl ether. Crystals deposit upon cooling. Filtration affords 20.8 g of the hydrazide, mp 160°-161.5°.

b. To 20.8 g of (1-benzyl-4-hydroxypiperidin-4-yl)acetic acid hydrazide (step a) in 120 ml water is added sufficient 10 N hydrochloric acid until the solution remains acid to litmus and the solid dissolves. The resulting solution is cooled to 10° and a solution of 6.3 g sodium nitrite in 60 ml water is added over five minutes. The solution is stirred five minutes at 10° and twenty minutes at 60°. The soluton is saturated with sodium chloride and then basified with 20% sodium hydroxide. Filtration affords 16.7 g 8-benzyl-1-oxa-3,8-diazaspiro[4.5]decan-2-one, mp 181°-182°.

PREPARATION 10

To a stirred mixture of 7 g lithium aluminum hydride and 150 ml tetrahydrofuran under argon is added dropwise over 20 minutes a solution of 24.6 g 8-benzyl-1-oxa-3,8-diazaspiro[4.5]decan-2-one in 150 ml tetrahydrofuran. The mixture is heated at reflux for two hours. The stirred mixture is treated with sequential dropwise addition of 7 ml water, 7 ml 15% sodium hydroxide, and 21 ml water. The mixture is filtered and the filter cake is washed with three 200 ml portions of dichloromethane. Evaporation of the combined filtrates affords 23 g of 1-benzyl-4-hydroxy-4-methylaminomethylpiperidine, an oil. A solution of 23 g 1-benzyl-4-hydroxy-4-methylaminomethylpiperidine and 250 ml dichloromethane is mixed with 100 ml of a 15% solution of phosgene in toluene. Evaporation of solvent gives a residue which is treated with 300 ml dichloromethane and 300 ml aqueous sodium bicarbonate. Separation of the dichloromethane layer followed by evaporation gives 20 g 3-methyl-3-benzyl-1-oxa-3,8-diazaspiro[4.5]decan-2-one, mp 137°-138°.

EXAMPLE 1

1. A mixture of 3.12 g 1-oxa-3,8-diazaspiro[4.5]decan-2-one, 5.4 g 2,3-epoxypropyl-o-methoxyphenyl ether, 5 ml methanol and 10 ml toluene is heated at reflux for 24 hours. The solvent is evaporated and the residue filtered through 20 g silica gel with 10% methanol/methylene chloride. Evaporation of solvent and crystallization from diethyl ether affords 4.6 g 8-[3-(2-methoxyphenoxy)-2-hydroxypropyl]-1-oxa-3,8-diazaspiro[4.5]decan-2-one, mp 124°-125°.

2. To a solution of 1 g of 8-[3-(2-methoxyphenoxy)-2-hydroxypropyl]-1-oxa-3,8-diazaspiro[4.5]decan-2-one in 5 ml methanol is added 10 ml, 3% hydrochloric acid in methanol. Addition of 200 ml diethyl ether followed by filtration affords 8-[3-(2-methoxyphenoxy)-2-hydroxypropyl]-1-oxa-3,8-diazaspiro[4.5]decan-2-one hydrochloride, mp indefinite.

Similarly prepared are the following:

3-methyl-8-[3-(2-methoxyphenoxy)-2-hydroxypropyl]-1-oxa-3,8-diazaspiro[4.5]decan-2-one hydrochloride, mp 153°-155°;

3-ethyl-8-[3-(2-methoxyphenoxy)-2-hydroxypropyl]-1-oxa-3,8-diazaspiro[4.5]decan-2-one hydrochloride, mp 162°-164°;

3-n-propyl-8-[3-(2-methoxyphenoxy)-2-hydroxypropyl]-1-oxa-3,8-diazaspiro[4.5]decan-2-one hydrochloride, mp 170°-171°;

3-isopropyl-8-[3-(2-methoxyphenoxy)-2-hydroxypropyl]-1-oxa-3,8-diazaspiro[4.5]decan-2-one hydrochloride, mp 135°-140°;

3-n-butyl-8-[3-(2-methoxyphenoxy)-2-hydroxypropyl]-1-oxa-3,8-diazaspiro[4.5]decan-2-one hydrochloride, mp 185°-190°;

3-benzyl-8-[3-(2-methoxyphenoxy)-2-hydroxypropyl]-1-oxa-3,8-diazaspiro[4.5]decan-2-one hydrochloride, mp 178°-180°;

3-(2-phenethyl)-8-[3-(2-methoxyphenoxy)-2-hydroxypropyl]-1-oxa-3,8-diazaspiro[4.5]decan-2-one hydrochloride, mp 152°-155°;

4,4-dimethyl-8-[3-(2-methoxyphenoxy)-2-hydroxypropyl]-1-oxa-3,8-diazaspiro[4.5]decan-2-one hydrochloride, mp indefinite;

4-phenyl-8-[3-(2-methoxyphenoxy)-2-hydroxypropyl]-1-oxa-3,8-diazaspiro[4.5]decan-2-one hydrochloride, mp 125°-134°; and 4-benzyl-8-[3-(2-methoxyphenoxy)-2-hydroxypropyl]-1-oxa-3,8-diazaspiro[4.5]decan-2-one hydrochloride, mp 90°-105°.

EXAMPLE 2

A mixture of 3.4 g 1-oxa-3,8-diazaspiro[4.5]decan-2-one, 2.26 g 2,3-epoxypropyl-p-methoxyphenyl ether, 5 ml methanol and 15 ml toluene is heated at reflux for 24 hours. Evaporation of solvent and recrystallization from ethyl acetate gives 2.7 g 8-[3-(4-methoxyphenoxy)-2-hydroxypropyl]-1-oxa-3,8-diazaspiro[4.5]decan-2-one, mp 151°-153°. To a solution of 1 g of 8-[3-(4-methoxyphenoxy)-2-hydroxypropyl]-1-oxa-3,8-diazaspiro[4.5]decan-2-one in 5 ml methanol is added 10 ml of 3% hydrochloric acid in methanol. Addition of 200 ml diethyl ether, followed by filtration gives 8-[3-(4-methoxyphenoxy)-2-hydroxypropyl]-1-oxa-3,8-diazaspiro[4.5]decan-2-one hydrochloride, mp 198°-203°.

EXAMPLE 3

A mixture of 1.7 g 1-oxa-3,8-diazaspiro[4.5]decan-2-one, 2 g 2-(1-hydroxy-2-bromoethyl)-1,4-benzodioxane [*J. Med. Chem.*, 13, 169 (1970)], 3 ml triethylamine and 5 ml N,N-dimethylformamide is heated at 90° for 18 hours. The mixture is poured into 100 ml water and the resulting mixture stirred for 10 minutes. The stirring is stopped and the aqueous layer decanted. The crude product is filtered through 20 g silica gel with 10% methanol-methylene chloride. Evaporation of the filtrate gives a residue which is taken up in 10 ml methanol. To this solution is added 10 ml of a 3% solution of hydrochloric acid in methanol. Addition of 200 ml of diethyl ether affords a precipitate which is collected by filtration, yielding 1.1 g (mixed erythro and threo) 8-[2-(1,4-benzodioxan-2-yl)-2-hydroxyethyl]-1-oxa-3,8-diazaspiro[4.5]decan-2-one hydrochloride, mp 235°-247° (d).

Similarly prepared are the following (erythro and threo mixtures):

3-methyl-8-[2-(1,4-benzodioxan-2-yl)-2-hydroxyethyl]-1-oxa-3,8-diazaspiro[4.5]decan-2-one hydrochloride, mp 230°-252° (d);

3-ethyl-8-[2-(1,4-benzodioxan-2-yl)-2-hydroxyethyl]-1-oxa-3,8-diazaspiro[4.5]decan-2-one hydrochloride, mp 220°-228° (d);

3-n-propyl-8-[2-(1,4-benzodioxan-2-yl)-2-hydroxyethyl]-1-oxa-3,8-diazaspiro[4.5]decan-2-one hydrochloride, mp 240°-244° (d);

3-isopropyl-8-[2-(1,4-benzodioxan-2-yl)-2-hydroxyethyl]-1-oxa-3,8-diazaspiro[4.5]decan-2-one hydrochloride, mp 245°-253° (d);

3-n-butyl-8-[2-(1,4-benzodioxan-2-yl)-2-hydroxyethyl]-1-oxa-3,8-diazaspiro[4.5]decan-2-one hydrochloride, mp 239°-244° (d);

3-n-benzyl-8-[2-(1,4-benzodioxan-2-yl)-2-hydroxyethyl]-1-oxa-3,8-diazaspiro[4.5]decan-2-one hydrochloride, mp 232°-255° (d);

3-(2-phenethyl)-8-[2-(1,4-benzodioxan-2-yl)-2-hydroxyethyl]-1-oxa-3,8-diazaspiro[4.5]decan-2-one hydrochloride, mp 215°-230° (d);

3-phenyl-8-[2-(1,4-benzodioxan-2-yl)-2-hydroxyethyl]-1-oxa-3,8-diazaspiro[4.5]decan-2-one hydrochloride, mp 217°-228° (d);

4-methyl-8-[2-(1,4-benzodioxan-2-yl)-2-hydroxyethyl]-1-oxa-3,8-diazaspiro[4.5]decan-2-one hydrochloride, mp 242°-250° (d);

4,4-dimethyl-8-[2-(1,4-benzodioxan-2-yl)-2-hydroxyethyl]-1-oxa-3,8-diazaspiro[4.5]decan-2-one hydrochloride, mp 165°-185° (d);

4-phenyl-8-[2-(1,4-benzodioxan-2-yl)-2-hydroxyethyl]-1-oxa-3,8-diazaspiro[4.5]decan-2-one hydrochloride, mp 158°-170° (d); and 4-benzyl-8-[2-(1,4-benzodioxan-2-yl)-2-hydroxyethyl]-1-oxa-3,8-diazaspiro[4.5]decan-2-one hydrochloride, mp 178°-190° (d).

EXAMPLE 4 a. A mixture of 2 g 1-oxa-3,8-diazaspiro[4.5]decan-2-one, 3.12 g 2,3-epoxypropyl 1-naphthyl ether, 5 ml methanol and 10 ml toluene is heated at reflux for 5 hours. The solvent is removed by evaporation in vacuum. The residue is filtered through 20 g silica gel with 5% methanol/methylene chloride. Evaporation of solvent and recrystalization from ethyl acetate affords 3.35 g 8-[3-(1-naphthyloxy)-2-hydroxypropyl]-1-oxa-3,8-diazaspiro[4.5]decan-2-one, mp 178°-179°.

Similarly prepared is 3-methyl-3-[3-(1-naphthyloxy)-2-hydroxypropyl]-1-oxa-3,8-diazaspiro[4.5]decan-2-one, mp 116°-117°.

b. To a solution of 1 g 8-[3-(1-naphthyloxy)-2-hydroxypropyl]-1-oxa-3,8-diazaspiro[4.5]decan-2-one in 5 ml methanol is added 10 ml 3% hydrochloric acid in methanol. Addition of 200 ml diethyl ether followed by filtration affords 8-[3-(1-naphthyloxy)-2-hydroxypropyl]-1-oxa-3,8-diazaspiro[4.5]decan-2-one hydrochoride, mp 137°-140°.

Similarly prepared is 3-methyl-8-[2-(1-naphthyloxy)-2-hydroxypropyl]-1-oxa-3,8-diazaspiro[4.5]decan-2-one hydrochloride, mp 241°-250° (d).

EXAMPLE 5

1.0 g of 8-[2-(1,4-benzodioxan-2-yl)-2-hydroxyethyl]-1-oxa-3,8-diazaspiro[4.5]decan-2-one is dissolved in a solution of 5 ml of diethyl ether and 5 ml of ethanol at 20°. To this solution is added 10 ml of a saturated solution of maleic acid in ethyl ether. The mixture is allowed to stand for one hour at room temperature. The resulting precipitate is recovered by filtration, washed three times with diethyl ether and then crystallized from a mixture to diethyl ether and ethanol affording 8-[2-(1,4-benzodioxan-2-yl)-2-hydroxyethyl]-1-oxa-3,8-diazaspiro[4.5]decan-2-one maleate.

Similarly, by following the same procedure, the corresponding maleate salts of the compounds of formula I are prepared.

What is claimed is:

1. A compound of the formula

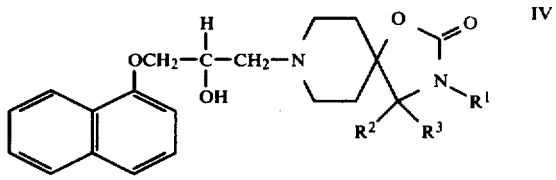

wherein $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety.

2. The compound of claim 1 wherein $R^1$, $R^2$ and $R^3$ are the same or different and are hydrogen, $C_1$ to $C_4$ alkyl, $C_6$ to $C_{12}$ carbo monocyclic or bicyclic aryl optionally mono- or disubstituted with methyl or ethyl, or aralkyl of 1 to 4 carbon atoms in the alkyl moiety and 6 to 10 carbon atoms in the aryl moiety.

3. The compound of claim 2 wherein $R^1$, $R^2$ and $R^3$ are the same or different and are hydrogen, methyl, ethyl, i-propyl, phenyl, naphthyl or the group $PhCH_2-$, $PhCH_2CH_2-$, $NaphCH_2-$ or $NaphCH_2CH_2-$.

4. The compound of claim 3 that is 8-[3-(1-naphthyloxy)-2-hydroxypropyl]-1-oxa-3,8-diazaspiro[4.5]decan-2-one.

5. The compound of claim 3 that is 3-methyl-8-[3-(1-naphthyloxy)-2-hydroxypropyl]-1-oxa-3,8-diazaspiro[4.5]decan-2-one.

6. The compound of claim 3 that is 3-ethyl-8-[3-(1-naphthyloxy)-2-hydroxypropyl]-1-oxa-3,8-diazaspiro[4.5]decan-2-one.

7. The compound of claim 3 that is 3-i-propyl-8-[3-(1-naphthyloxy)-2-hydroxypropyl]-1-oxa-3,8-diazaspiro[4.5]decan-2-one.

8. A compound of the formula

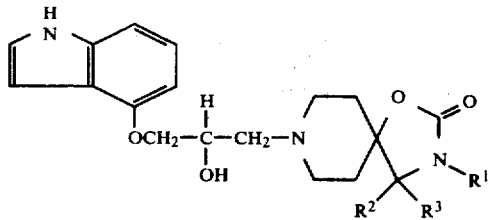

where $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety.

9. The compound of claim 8 wherein $R^1$, $R^2$ and $R^3$ are the same or different and are hydrogen, $C_1$ to $C_4$ alkyl, $C_6$ to $C_{12}$ carbo monocyclic or bicyclic aryl optionally mono- or disubstituted with methyl or ethyl, or aralkyl of 1 to 4 carbon atoms in the alkyl moiety and 6 to 10 carbon atoms in the aryl moiety.

10. The compound of claim 9 wherein $R^1$, $R^2$ and $R^3$ are the same or different and are hydrogen, methyl, ethyl, i-propyl, phenyl, naphthyl or the group PhCH$_2$—, PhCH$_2$CH$_2$—, NaphCH$_2$— or NaphCH$_2$CH$_2$—.

11. The compound of claim 10 that is 8-[3-(4-indolyloxy)-2-hydroxypropyl]-1-oxa-3,8-diazaspiro[4.5]decan-2-one.

12. The compound of claim 10 that is 3-methyl-8-[3-(4-indolyloxy)-2-hydroxypropyl]-1-oxa-3,8-diazaspiro[4.5]decan-2-one.

13. The compound of claim 10 that is 3-ethyl-8-[3-(4-indolyloxy)-2-hydroxypropyl]-1-oxa-3,8-diazaspiro[4.5]decan-2-one.

14. The compound of claim 10 that is 3-i-propyl-8-[3-(4-indolyloxy)-2-hydroxypropyl]-1-oxa-3,8-diazaspiro[4.5]decan-2-one.

15. A compound of the formula

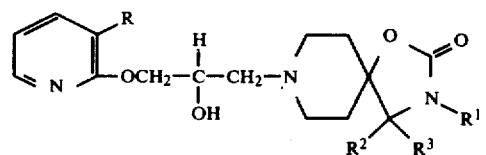

where R is $C_1$ to $C_8$ alkyl, $C_1$ to $C_8$ alkoxy, halo, cyano, AlkNHC(O)— or AlkC(O)NH— where Alk is $C_1$ to $C_6$ alkyl and $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety.

16. The compound of claim 15 wherein R is hydrogen or cyano.

17. The compound of claim 16 wherein $R^1$, $R^2$ and $R^3$ are the same or different and are hydrogen, $C_1$ to $C_4$ alkyl, $C_6$ to $C_{12}$ carbo monocyclic or bicyclic aryl optionally mono- or disubstituted with methyl or ethyl, or aralkyl of 1 to 4 carbon atoms in the alkyl moiety and 6 to 10 carbon atoms in the aryl moiety.

18. The compound of claim 17 wherein $R^1$, $R^2$ and $R^3$ are the same or different and are hydrogen, methyl, ethyl, i-propyl, phenyl, naphthyl or the group PhCH$_2$—, PhCH$_2$CH$_2$—, NaphCH$_2$— or NaphCH$_2$CH$_2$—.

19. The compound of claim 18 that is 8-[3-(3-cyano-2-pyridyloxy)-2-hydroxypropyl]-1-oxa-3,8-diazaspiro[4,5]decan-2-one.

20. The compound of claim 18 that is 3-methyl-8-[3-(3-cyano-2-pyridyloxy)-2-hydroxypropyl]-1-oxa-3,8-diazaspiro[4.5]decan-2-one.

21. The compound of claim 18 that is 3-ethyl-8-[3-(3-cyano-2-pyridyloxy)-2-hydroxypropyl]-1-oxa-3,8-diazaspiro[4.5]decan-2-one.

22. The compound of claim 18 that is 3-i-propyl[3-(3-cyano-2-pyridyloxy)-2-hydroxypropyl]-1-oxa-3,8-diazaspiro[4.5]decan-2-one.

23. A compound of the formula

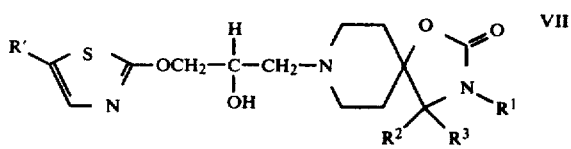

wherein R' is AlkNHC(O)— or AlkC(O)NH— where Alk is $C_1$ to $C_6$ alkyl and $R^1$, $R^2$ and $R^3$ are the same or different and are hydrogen, $C_1$ to $C_6$ alkyl, $C_6$ to $C_{14}$ carbocyclic aryl or aralkyl of 1 to 6 carbon atoms in the alkyl moiety and 6 to 12 carbon atoms in the carbocyclic aryl moiety.

24. The compound of claim 23 wherein R' is AlkNHC(O)— or AlkC(O)NH— where Alk is $C_1$ to $C_6$ alkyl or the group 2-(endobicyclo[3.1.0]he;xyl)ethyl.

25. The compound of claim 24 wherein Alk is $C_1$ to $C_4$ alkyl or the group 2-(endobicyclo[3.1.0]hexyl)ethyl and $R^1$, $R^2$ and $R^3$ are the same or different and are hydrogen, $C_1$ to $C_4$ alkyl, $C_6$ to $C_{12}$ carbo monocyclic or bicyclic aryl optionally mono- or disubstituted with methyl or ethyl, or aralkyl of 1 to 4 carbon atoms in the alkyl moiety and 6 to 10 carbon atoms in the aryl moiety.

26. The compound of claim 25 wherein Alk is 2-(endobicyclo[3.1.0]hexyl)ethyl, hydrogen, methyl, ethyl or i-propyl and $R^1$, $R^2$ and $R^3$ are the same or different and are methyl, ethyl, i-propyl, phenyl, naphthyl or the group PhCH$_2$—, PhCH$_2$CH$_2$—, NaphCH$_2$— or NaphCH$_2$CH$_2$—.

27. The compound of claim 26 that is 8-[3-(5-[2-(endobicyclo[3.1.0]hexyl)ethyl]carboxamido-2-thiazoloxy)-2-hydroxypropyl]-1-oxa-3,8-diazaspiro[4.5]decan-2-one.

28. The compound of claim 26 that is 3-methyl-8-[3-(5-[2-(endobicyclo[3.1.0]hexyl)ethyl]carboxamido-2-thiazoloxy)-2-hydroxypropyl]-1-oxa-3,8-diazaspiro[4.5]decan-2-one.

29. The compound of claim 26 that is 3-ethyl-8-[3-(5-[2-(endobicyclo[3.1.0]hexyl)ethyl]carboxamido-2-thiazoloxy)-2-hydroxypropyl]-1-oxa-3,8-diazaspiro[4.5]decan-2-one.

30. The compound of claim 26 that is 3-i-propyl-8-[3-(5-[2-(endobicyclo[3.1.0]hexyl)ethyl]carboxamido-2-thiazoloxy)-2-hydroxypropyl]-1-oxa-3,8-diazaspiro[4.5]decan-2-one.

31. A pharmaceutical composition useful for treating hypertension and cardiac disorders containing as the active agent a compound according to claim 1, 8, 15 or 23 in a physiologically active amount and a non-toxic, pharmaceutically acceptable carrier.

32. A method for treating hypertension and cardiac disorders in mammals consisting of administering to said mammals an amount effective therefor of a compound according to claim 1, 8, 15 or 23.

* * * * *